United States Patent
Hagedorn et al.

(10) Patent No.: US 11,324,672 B2
(45) Date of Patent: May 10, 2022

(54) METHOD FOR PREPARING HYALURONIC ACID DERMAL FILLERS, DERMAL FILLERS OBTAINED THEREBY AND THEIR USE

(71) Applicant: Merz Pharma GmbH & Co. KGaA, Frankfurt am Main (DE)

(72) Inventors: Nadine Hagedorn, Frankfurt am Main (DE); Roland Stragies, Berlin (DE); Lubin Belkovi, Friedrichsdorf (DE); Radia El-Banna, Bad Vilbel-Gronau (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 0 days.

(21) Appl. No.: 16/344,941

(22) PCT Filed: Nov. 2, 2017

(86) PCT No.: PCT/EP2017/078094
§ 371 (c)(1),
(2) Date: Apr. 25, 2019

(87) PCT Pub. No.: WO2018/083195
PCT Pub. Date: May 11, 2018

(65) Prior Publication Data
US 2019/0269582 A1    Sep. 5, 2019

(30) Foreign Application Priority Data
Nov. 3, 2016 (EP) .................... 16197109

(51) Int. Cl.
*A61K 8/20* (2006.01)
*A61K 8/04* (2006.01)
*A61K 8/24* (2006.01)
*A61K 8/73* (2006.01)
*A61Q 19/00* (2006.01)
*A61Q 19/08* (2006.01)

(52) U.S. Cl.
CPC ............... *A61K 8/042* (2013.01); *A61K 8/20* (2013.01); *A61K 8/24* (2013.01); *A61K 8/735* (2013.01); *A61Q 19/001* (2013.01); *A61Q 19/08* (2013.01); *A61K 2800/805* (2013.01); *A61K 2800/91* (2013.01)

(58) Field of Classification Search
None
See application file for complete search history.

(56) References Cited

U.S. PATENT DOCUMENTS

| 8,052,990 B2 | 11/2011 | Hermitte et al. |
| 9,822,723 B2 | 11/2017 | Barg et al. |
| 2013/0102563 A1 | 4/2013 | Lebreton |
| 2015/0366976 A1 | 12/2015 | Nguyen et al. |
| 2017/0143870 A1 | 5/2017 | Linko et al. |

FOREIGN PATENT DOCUMENTS

| WO | 2005/085329 A1 | 9/2005 | |
| WO | 2013/185934 A1 | 12/2013 | |
| WO | WO 2013/185934 | * 12/2013 | ............. C08B 37/08 |
| WO | 2014/064633 A1 | 5/2014 | |
| WO | 2014064633 A1 | 5/2014 | |
| WO | 2014/198406 A1 | 12/2014 | |
| WO | 2015/149941 A1 | 10/2015 | |
| WO | 2016/096920 A1 | 6/2016 | |

OTHER PUBLICATIONS

PCT International Search Report for PCT/EP2017/078094, dated Dec. 1, 2017.

* cited by examiner

*Primary Examiner* — Craig D Ricci
(74) *Attorney, Agent, or Firm* — McBee Moore & Vanik IP, LLC

(57) ABSTRACT

The present invention generally relates to the field of hyaluronic acid (HA) dermal fillers, and more specifically to methods for preparing crosslinked HA-based compositions in the form of a gel comprising high-temperature dialysis and/or crosslinking in the presence of phosphate and an alkaline metal halide salt. The present invention further relates to crosslinked HA-based gel compositions prepared by said methods and their use as dermal fillers in aesthetic applications such as wrinkle treatments.

9 Claims, No Drawings

METHOD FOR PREPARING HYALURONIC ACID DERMAL FILLERS, DERMAL FILLERS OBTAINED THEREBY AND THEIR USE

FIELD OF THE INVENTION

The present invention generally relates to the field of hyaluronic add (HA) dermal fillers, and more specifically to methods for preparing crosslinked HA-based compositions in the form of a gel comprising high-temperature dialysis and/or crosslinking in the presence of phosphate and an alkaline metal halide salt. The present invention further relates to crosslinked HA-based gel compositions prepared by said methods and their use as dermal fillers in aesthetic applications such as wrinkle treatments.

BACKGROUND OF THE INVENTION

Nonsurgical rejuvenation procedures using injectable dermal fillers are currently considered to be the second most common non-surgical aesthetic treatments performed worldwide, behind botulinum toxin injections. While there are numerous filler types available to the clinician, hyaluronic acid is by far the most commonly utilized filler material today.

Hyaluronic acid is a natural polysaccharide composed of linked repeating units of N-acetyl-D-glucosamine and D-glucuronic acid. It is found throughout the human body (e.g., in the skin) and generally well tolerated and safe. Because of its ability to bind and hold water, hyaluronic acid also play a supportive role in in skin hydration. Furthermore, hyaluronic acid exhibits excellent viscoelastic properties and has a high tissue-lifting capacity (volumizing effect), making hyaluronic acid the dermal filler material of choice.

Unfortunately, hyaluronic acid is rapidly degraded in vivo by enzymatic and free radical degradation, and it has an in vivo half-life of only about 24-48 hours. Therefore, in most commercial products, hyaluronic acid is crosslinked to increase its longevity. While many different crosslinking agents have been investigated and used in crosslinked hyaluronic acid products, 1,4-butanediol diglycidyl ether (BDDE) is today the most commonly used crosslinking agent.

However, although BDDE represents the "gold standard", it has some disadvantages. For example, any BDDE-crosslinked HA product will always contain unreacted (i.e. "free") BDDE as well as partially hydrolyzed BDDE (i.e. epoxydioles; EPD) and BDDE degradation products like 2,6-dimethylaniline (DMA). BDDE and EPD contain reactive epoxide groups and are therefore, like DMA, generally considered toxic, and BDDE is even suspected of being carcinogenic.

In view of the above, the amount of compounds such as BDDE, EPD and DMA in the final product needs to be strictly controlled to a low level in order to achieve the desired safety profile and to fulfill regulatory requirements. However, the purification procedures used today for removing said unwanted impurities from the gel are not entirely satisfying. For example, dialysis is often inadequate in terms of cost and labor requirements, purification efficiency and/or purification time.

Furthermore, the currently employed crosslinking processes using BDDE as crosslinker are commonly carried out using a relatively high amount of BDDE in an attempt to achieve the desired degree of crosslinking and rheological properties of the final HA-based gel. Undesirably, this results in relatively high amounts of toxic BDDE, EPD and DMA in the gel. Accordingly, there is a great interest in a highly effective crosslinking method, which allows for the use of reduced amounts of BDDE while still achieving the same rheological properties, thereby decreasing the amount of unwanted impurities, e.g. BDDE, EPD and DMA, in the gel.

WO 2014/064633 discloses crosslinking of HA in the presence of at least one alkali halide salt in a concentration of between 0.5% and 20% which makes it possible to improve the rheological properties of a crosslinked HA gel. Furthermore, WO 2013/185934 discloses crosslinking of HA in the presence of a phosphate buffer, leading to a HA gel implant suitable for increasing the volume of skin tissue. Despite these efforts, there is a continuing need for an improved HA crosslinking method that employs less BDDE, resulting in lower amounts of unreacted BDDE and degradation products thereof in the final product.

OBJECT OF THE INVENTION

Having regard to the above, it is an object of the present invention to provide a method for the preparation of crosslinked hyaluronic acid (HA) gels having a decreased amount of unwanted impurities while providing desirable properties for use as dermal filler.

SUMMARY OF THE INVENTION

The above object is achieved by the provision of a high temperature dialysis procedure having an increased rate and efficiency of dialysis of hyaluronic acid (HA)-based gels, and the provision of a highly efficient method for crosslinking of hyaluronic acid (HA)-based composition using a phosphate buffer as crosslinking reaction medium.

In a first aspect, the present invention provides a method for preparing a hyaluronic acid (HA) dermal filler comprising the steps of:
(a) providing a crosslinked hyaluronic acid (HA)-based composition in the form of a gel, the HA being crosslinked with an epoxide crosslinking agent, and
(b) dialyzing the crosslinked HA-based gel, wherein the dialysis is carried out at a temperature of at least 20° C.

The dialysis at elevated temperatures ("high temperature dialysis") results in an improved rate and efficiency of dialysis. This advantageously allows for the reduction of the dialysis time required to achieve a specified level of impurities. Preferably, the dialysis is carried out at a temperature of at least 10° C., at least 15° C., at least 20° C., at least 25° C., or at least 30° C., more preferably at a temperature of at least 35° C. or at least 40° C., and most preferably at a temperature of at least 45° C. or at least 50° C.

In a second aspect, the present invention provides a method for preparing a hyaluronic acid (HA) dermal filler comprising the steps of:
(a) providing a composition comprising water, non-crosslinked HA and at least one epoxide crosslinking agent, and
(b) reacting the composition under conditions that allow crosslinking the non-crosslinked HA to form a crosslinked HA-based composition in the form of a gel,
wherein said composition further comprises at least one alkali metal halide salt and phosphate, the phosphate being provided by at least one phosphate salt and optionally phosphoric acid, wherein the phosphate salt is an alkali metal phosphate salt, an alkaline earth metal phosphate salt, or a combination thereof.

The crosslinking in the presence of phosphate and an alkali metal halide salt results in an increased efficiency of crosslinking, which makes it possible to use less crosslinking agent and/or lower HA concentrations while maintaining the desired rheological properties of the final gel product.

In a third aspect, the present invention provides a hyaluronic acid (HA) dermal filler prepared by the method according to the first and/or second aspect of the present invention. The thus obtained HA-based gel contains very low amounts of unwanted impurities like residual non-reacted epoxide crosslinker or partially reacted epoxide crosslinker or degradation products thereof. Thus, it exhibits a very favorable safety profile.

In a fourth aspect, the present invention provides a kit comprising a hyaluronic acid (HA) dermal filler according to the present invention, and optionally instructions for use.

The kit preferably contains at least one pre-filled syringe containing the HA-based gel according to the first or second aspect of the present invention, and optionally instructions for use. The kit is suitable for use in various cosmetic (aesthetic) treatments.

In a fifth aspect, the present invention relates to the use of a hyaluronic acid (HA) dermal filler according to the present invention for cosmetic applications.

Non-limiting cosmetic applications include cosmetic treatments of facial lines, facial wrinkles, glabellar lines, nasolabial folds, marionette lines, buccal commissures, perilip wrinkles, crow's feet, subdermal support of the brows, malar and buccal fat pads, tear troughs, nose, lips, cheeks, peroral region, infraorbital region, facial asymmetries, jawlines, and chin.

In a sixth aspect, the present invention provides a method for replacing or filling of a biological tissue or increasing the volume of a biological tissue for cosmetic purposes, in particular for cosmetic treatments of skin lines and wrinkles, comprising administering to a subject in need thereof an effective amount of the hyaluronic acid (HA) dermal filler according to the present invention.

Preferred embodiments of the present invention are set forth in the appended claims. Further embodiments and other objects, advantages and features of the present invention will become apparent from the following detailed description of the invention and the examples.

DETAILED DESCRIPTION OF THE INVENTION

It was surprisingly found that dialysis of a hyaluronic acid (HA)-based gel at elevated temperatures (e.g. at a temperature of at least 30° C. or at least 45° C.) exhibits a much higher rate and efficiency than standard dialysis performed at low temperature (e.g. at 5-8° C.) and that the HA-based gel remains stable despite the relatively high temperature used during dialysis. It was further found that the crosslinking of HA with an epoxide crosslinking agent in the presence of phosphate and at least one alkaline metal halide salt (e.g., lithium chloride) unexpectedly results in a significantly improved modulus of elasticity (G'). This allows for the use of less epoxide crosslinking agent which, like the high temperature dialysis, makes it possible to prepare crosslinked HA gels containing decreased levels of unwanted residual epoxide crosslinker and degradation products thereof.

As used herein, the term "dermal filler" generally refers to a material designed to add volume to, or replace or augment volume of, soft tissue areas of skin. The dermal filler described herein is normally sterile and generally injectable, i.e. can be dispensed from syringes or similar devices under normal conditions under normal pressure to the desired target site (e.g., in the dermis and hypodermis).

The term "gel", as used herein, usually refers to a material having fluidity at room or body temperature between that of a liquid and solid. Since it is generally capable of absorbing water it may also be referred to as "hydrogel" herein. The gel is preferably "cohesive", which means that the gel has the capacity not to dissociate because of the affinity of its molecules for each other. Cohesivity is important with regard to gel integrity and, for the purpose of the present invention, can be determined using the Gavard-Sundaram Cohesivity (GSC) scale (Sundaram et al., Plast. Reconstr. Surg. 136:678-686, 2015). Preferably, the dermal filler of the present invention has a cohesivity of 3, 4 or 5 on the five-point GSC scale.

The term "hyaluronic acid" or "HA", as used herein, includes hyaluronic acid, hyaluronate, and any of its hyaluronate salts, such as salts of hyaluronate and sodium, potassium, lithium, magnesium, calcium, or combinations thereof. The term "non-crosslinked", as used herein, refers to HA molecules that are not crosslinked, or very lightly crosslinked (very low degree of crosslinking or essentially uncrosslinked, e.g., a degree of modification of less than 1% or less than 0.1%).

Furthermore, the term "comprise", as used herein, for example in the context of "a composition comprising . . ." or "a method comprising . . .", is intended to encompass both the open-ended term "includes" and the closed-ended phrase "consisting of".

In a first aspect, the present invention provides a method for preparing a hyaluronic acid (HA) dermal filler comprising the steps of:

(a) providing a crosslinked hyaluronic acid (HA)-based composition in the form of a gel, the HA being crosslinked with an epoxide crosslinking agent, and (b) dialyzing the crosslinked HA-based gel, wherein the dialysis is carried out at a temperature of at least 20° C.

In step (a), the provided crosslinked HA-based composition is not particularly restricted and includes, e.g., mono-crosslinked (i.e. crosslinked in a single crosslinking reaction), double-crosslinked and triple-crosslinked HAs, as disclosed in, e.g., WO 2005/085329 (polydensified HA gels) and WO 2014/198406 A1 (triple-crosslinked HA gels).

The term "epoxide crosslinking agent", as used herein, refers to a diepoxide or a multiepoxide crosslinking agent, i.e. a crosslinking agent having two or more epoxide functional groups capable of reacting with polysaccharide polymers (e.g., hyaluronic acid) to form covalent (intra- and/or intermolecular) crosslinks. Preferably, the crosslinker is a diepoxide crosslinker such as 1,4-butanediol diglycidyl ether (BDDE), ethylene glycol diglycidyl ether (EGDGE), 1,6-hexanediol diglycidyl ether, polyethylene glycol diglycidyl ether, polypropylene glycol diglycidyl ether, polytetramethylene glycol digylcidyl ether, neopentyl glycol digylcidyl ether, polyglycerol polyglycidyl ether, 1,2,7,8-diepoxyoctane, 3-(bis(glycidoxymethyl)-methoxy)-1,2-propanediol, 1,4-cyclohexanedimethanol diglycidyl ether, 4-vinyl-1-cyclohexene diepoxide, 1,2,5,6-diepoxycyclooctane, and bisphenol A diglycidyl ether. Particularly preferred for use herein is 1,4-butanediol diglycidyl ether (BDDE).

Within the context of the present invention, the molecular mass of HA is not particularly limited and may be, for example, between $2.0 \times 10^5$ Da and $5.0 \times 10^6$ Da, preferably between $5.0 \times 10^5$ Da and $4.0 \times 10^6$ Da, more preferably between $1.0 \times 10^6$ Da and $3.5 \times 10^6$ Da, and most preferably between $2.0 \times 10^6$ Da and $3.0 \times 10^6$ Da. The HA may also comprise a mixture of high molecular weight HA having a molecular weight of, e.g., $2.0 \times 10^6$ Da to $4.0 \times 10^6$ Da, and a low molecular weight HA having a molecular weight of, e.g., $0.2 \times 10^6$ Da to $1.0 \times 10^6$ Da, in a ratio of, e.g., between 10:90 to 90:10.

Reference to "molecular weight" or "molecular mass" of HA are, for the purpose of the present invention, to be understood as indicating the viscosity average molecular mass ($M_v$). The viscosity average molecular mass can be calculated by relating the measured intrinsic viscosity ($\eta$) to the average molecular weight ($M_v$) by the following Mark-Houwink equation: $[\eta] = K \times M_v^a$, wherein $[\eta]$=intrinsic viscosity in $m^3/kg$, Mv=molecular mass, $K=2.26 \times 10^{-5}$ $m^3/kg$, and a=0.796. The intrinsic viscosity is may be measured at 25° C. using a buffer solution of 0.15 M sodium chloride in 0.01 M phosphate buffer solution (pH 7.0) by means of a suspended level viscometer (Ubbelohde type viscometer) according to the procedure defined in European Pharmacopoeia 7.0 (see sodium hyaluronate monograph 01/2011: 1472).

The degree of modification (MoD) of the crosslinked HA in the dermal filler composition, expressed as the ratio of the sum of mono- and double-crosslinked epoxide crosslinkers (e.g. BDDE crosslinkers) to the sum of HA repeating disaccharide units, is preferably from 0.5% to 50%, from 1% to 20%, from 5% to 15%, or about 10%. The degree of modification can be determined by NMR in accordance with methods known in the art (Edsman et al., Gel Properties of Hyaluronic Acid Dermal Fillers, Dermatol. Surg. 2012, 38:1170-1179; Guarise et al., SEC determination of crosslink efficiency in hyaluronan fillers, Carbohydrate Polymers 2012, 88:428-434; Kenne et al., Modification and crosslinking parameters in hyaluronic acid hydrogels—Definitions and analytical methods, Carbohydrate Polymers 2013, 91:410-418).

In step (b), the dialysis is preferably carried out at a temperature of at least 10° C. or at least 15° C. or at least 20° C. or at least 25° C. or at least 30° C., more preferably at a temperature of at least 35° C. or at least 40° C., and most preferably at a temperature of at least 45° C. or at least 50° C. The upper limit is determined by the tendency of HA gels to degrade at excessively high temperatures. Those skilled in the art will be readily able to select appropriate temperatures to limit degradation to an acceptable level. Although not intended to be limiting, the upper temperature limit may be, for example, 60° C., 65° C., 70° C., 75° C. or 80° C. Thus, exemplary suitable temperature ranges are 10° C. to 80° C., 15° C. to 80° C., 20° C. to 80° C., 25° C. to 80° C., 30° C. to 80° C., or 35° C. to 75° C., or 40° C. to 70° C., or 45° C. to 65° C., or 50° C. to 60° C., in particular 20° C. to 65° C. or 30° C. to 60° C.

The dialysis buffer used in dialysis commonly has a pH of about 6.2 to 7.9, particularly a pH of about 6.5 to 7.8, more particularly a pH of about 6.8 to 7.4. The buffer used may be a phosphate buffer, and in particular a phosphate buffer with a pH within the ranges mentioned above. Suitable phosphate buffers preferably have a phosphate concentration of about 0.01 mM to about 120 mM, more preferably from about 0.1 mM to about 100 mM, and most preferably from about 1.0 mM to about 75 mM.

Within the context of the present invention, the phosphate concentration refers to the total concentration of all phosphate species (i.e. $PO_4^{3-}$, $HPO_4^{2-}$, $H_2PO_4^-$, $H_3PO_4$) present in the dialysis buffer. It is calculated as the total amount (in moles) of phosphate salts, and optionally phosphoric acid, added to the dialysis buffer divided by the volume of the dialysis buffer (in litres) and expressed in mM or M.

In addition, the dialysis buffer, especially the phosphate buffer described above, generally has an osmolality in the range of 200 to 400 mOsm, particularly in the range of 250 mOsm/kg to 350 mOsm/kg. If the dialysis buffer is a phosphate buffer, it preferably contains sodium chloride in an amount so that the osmolality of the dialysis buffer is between about 220 mOsm/kg and about 390 mOsm/kg, more preferably between about 250 mOsm/kg and about 350 mOsm/kg, and most preferably between about 270 mOsm/kg and about 300 mOsm/kg.

Generally, the dialysis is carried out for 6 h to 96 h, typically for about 20 h to 50 h. The volume of dialysis buffer is commonly at least 50-fold, preferably at least 75-fold to 200-fold, the volume of the gel sample to be dialyzed. Further, the dialysis buffer is generally exchanged at least once, usually two, three, four, five or six times, particularly two or three times. Other suitable conditions for dialysis will be readily apparent to those skilled in the art.

The hyaluronic acid (HA) dermal filler of the present invention (i.e. the HA dermal filler prepared according to the first aspect and second aspect of the present invention) generally contains crosslinked HA in an amount of between 1 mg/ml and 50 mg/ml, preferably between 5 mg/ml to 40 mg/ml, more preferably between 10 mg/ml and 35 mg/ml, still more preferably between 15 mg/ml and 30 mg/ml, and most preferably between 20 mg/ml and 25 mg/ml.

Preferably, the method according to the first aspect of the present invention may further comprise step (c) of sterilizing the crosslinked HA gel. This step may be carried out by subjecting the crosslinked HA gel to sterilization by moist heat, such as at a temperature of 121 to 130° C. for 1 to 20 minutes, e.g. at 121° C. for 5 minutes. Typically, the crosslinked HA gel is filled into a syringe which is then sterilized as described. Those skilled in the art know how to select appropriate sterilization conditions so as to obtain the desired result.

Furthermore, the method of the present invention may comprise additional step(s) of adding optional compounds or substances resulting in a HA dermal filler comprising said optional compounds or substances. Inn particular, the HA dermal filler composition prepared according to the present invention (i.e. according to the method of the first aspect and second aspect of the present invention) may further comprise non-crosslinked HA, for example as a lubricant to improve the filler's rheological properties, such as to lower its extrusion force. The molecular weight of the non-crosslinked HA is preferably between $3.0 \times 10^5$ Da and $4.0 \times 10^6$ Da, in particular between $1.0 \times 10^6$ Da and $3.0 \times 10^6$ Da.

The amount of non-crosslinked HA present in the dermal filler is not specifically limited but is preferably from 0.001 mg/g to 100 mg/g, in particular from 0.1 mg/g to 50 mg/g, and more particularly from 1 mg/g to 10 mg/g. Alternatively, the dermal filler of the present invention may also be free of any added non-crosslinked HA, i.e. being devoid or essentially devoid of any non-crosslinked HA.

Furthermore, the dermal filler may optionally comprise an anesthetic, particularly a local anesthetic. The anesthetic is added for reducing pain caused by injection of the dermal filler. Generally, the total amount of anesthetic agent(s) included in the dermal filler is in the range of 0.01 wt. % to 5 wt. % and, in particular, in the range of 0.1 wt. % to 2 wt. %.

Suitable local anesthetics for use herein include, but are not limited to, ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethysoquin, dimethocaine, diperodon, dycyclonine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, psuedococaine, pyrrocaine, ropivacaine, salicyl alcohol, tetracaine, tolycaine, trimecaine, zolamine, and salts thereof. Combinations of two or more of the mentioned anesthetic agents, for example a combination of lidocaine and other "caine"-anesthetic(s) like prilocaine, may also be used herein.

Preferably, the at least one anesthetic agent is lidocaine or a salt thereof, such as lidocaine hydrochloride (lidocaine HCl). The lidocaine concentration in the dermal filler described herein may be in the range of 0.05 wt. % to 5 wt. %, for example, from 0.1 wt. % to 2.0 wt. % or from 0.2% to 1.0 wt. %. Preferably, the lidocaine concentration is about 0.3 wt. %.

The dermal filler composition of the present invention may further comprise no more than 10 wt. %, for example no more than 5 wt. %, of one or more compounds selected from the group consisting of antioxidants (e.g., ascorbic acid and derivatives thereof, tocopherols, carotenoids and derivatives thereof, retinol, glutathione, and ubiquinones), amino acids (e.g., proline, lysine, arginine, leucine, isoleucine, and methionine), metal salts (e.g., a zinc salt), hydroxyapatite particles (e.g., calcium hydroxyapatite particles, preferably having a mean diameter of less than about 200 µm, e.g., 10 µm to 80 µm), polyols (e.g., glycerol, mannitol, sorbitol, propylene glycol, erythritol, xylitol, maltitol, and lactitol), vitamins (e.g., vitamin C, vitamin E and vitamins of the B group), and one or more crosslinked and/or non-crosslinked polysaccharide other than HA (e.g. heparosan or a cellulose derivative like carboxymethyl cellulose (CMC)). In one embodiment, the dermal filler composition does not contain any of the one or more compounds mentioned in this paragraph.

In a second aspect, the present invention relates to a method for preparing a hyaluronic acid (HA) dermal filler comprising the steps of:
  (a) providing a composition comprising water, non-crosslinked HA and at least one epoxide crosslinking agent, and
  (b) reacting the composition under conditions that allow crosslinking the non-crosslinked HA to form a crosslinked HA-based composition in the form of a gel,
wherein said composition further comprises at least one alkali metal halide salt and phosphate. The phosphate is provided by at least one phosphate salt, and optionally phosphoric acid, and is an alkali metal phosphate salt, an alkaline earth metal phosphate salt, or a combination thereof. Preferably, the phosphate salt is an alkali metal phosphate salt.

Examples of suitable alkali metal phosphate salts for use herein include salts of phosphate and lithium, sodium, potassium, or a combination thereof. Preferably, the alkali metal phosphate salt is a salt of phosphate and sodium, potassium, or a combination thereof, in particular a salt of phosphate and sodium. The alkaline earth metal phosphate salt is preferably a phosphate salt of magnesium, calcium, or a combination thereof.

Suitable alkaline metal halide salts for use herein include those in which the alkali metal of the halide salt is lithium, sodium, potassium, or a combination thereof, particularly lithium, sodium, or a combination thereof, and more particularly lithium. The halogen of suitable halide salts for use herein include fluorine, chlorine, bromine or iodine, or a combination thereof, particularly chlorine, bromine, or a combination thereof, more particularly chlorine. Particular preferred for use herein is lithium chloride (LiCl), sodium chloride (NaCl) and potassium chloride (KCl), or a combination thereof. Most preferred is lithium chloride (LiCl).

The amount of the at least one halide salt in the composition provided in step (a) and/or subjected to crosslinking in step (b) is typically less than 0.5 wt. % and may be less than 0.45, 0.40, 0.30, 0.20 or 0.10 wt. %, particularly less than 0.09, 0.08, 0.07, 0.06 wt. %, more particularly less than 0.05, 0.04, 0.03, 0.02 or 0.01 wt. %. The lower limit of the amount of the at least halide salt in said composition is not specifically limited and can be readily determined by those skilled in the art. For example, the lower limit may be defined as that amount of the at least one halide salt that results in an increase in the elastic modulus (G') of the final crosslinked HA dermal filler after sterilization of at least 5%, as compared to before sterilization. The lower limit may be, e.g., 0.001 wt. % or 0.005 wt. %.

Preferably, the amount of the at least one halide salt is within the range of 0.01 wt. % to less than 0.5 wt. %, 0.02 wt. % to 0.45 wt. %, 0.03 wt. % to 0.4 wt. %, 0.04 wt. % to 0.3 wt. %, 0.05 wt. % to 0.2 wt. %, 0.06 wt. % to 0.15 wt. %, or 0.07 wt. % to 0.10 wt. %.

The amount of phosphate in the composition provided in step (a) and/or subjected to crosslinking in step (b) is generally from 0.001 wt. % to 5 wt. %, particularly from 0.01 wt. % to 2.5 wt. %, more particularly from 0.1 wt. % to 2.0 wt. % or from 0.25 wt. % to 1.5 wt. % or from 0.5 wt. % to 1.0 wt. %. Within the framework of the present invention, the amount of phosphate is calculated as the total amount of said at least one phosphate salt and phosphoric acid (source of phosphate) added to the composition.

In step (b), the crosslinking is commonly carried out under conditions of a temperature ($T_x$) of at least 25° C., particularly at least 30° C. or at least 40° C., wherein the temperature ($T_x$) and the crosslinking time ($t_x$) preferably satisfy the equation: $(T_x)^2 t_x = y$, with y being in the range of from $2 \times 10^4$ (° C.)$^2 \cdot$h to $2 \times 10^5$ (° C.)$^2 \cdot$h, in particular in the range of $1 \times 10^4$ (° C.)$^2 \cdot$h to $3 \times 10^5$ (° C.)$^2 \cdot$h. The crosslinking temperature is preferably in the range of 25° C. to 70-80° C., in particular in the range of 30° C. to 60° C., 35° C. to 55° C. or 40° C. to 50° C. Furthermore, the crosslinking pH may be at least 10.0, at least 11.0, at least 12.0 or at least 13.0.

The concentration of HA during crosslinking (i.e. in the composition provided in step (a)) is typically between 50 mg/ml and 150 mg/ml, particularly between 75 mg/ml and 125 mg/ml, more particularly about 100 mg/ml. The degree of crosslinking, expressed as the weight ratio of epoxide crosslinking agent (e.g., BDDE) present in the aqueous mixture provided in step (a) and subjected to crosslinking in step (b) to repeating disaccharide units of HA present in the aqueous mixture provided in step (a) and subjected to crosslinking in step (b) may be in the range of 1% to 20% and is usually in the range of 4% to 12% or 6% to 10%.

After crosslinking, the reaction mixture obtained from step (b) is generally neutralized by adding an appropriate amount of an aqueous solution containing an acid or base. For example, a solution of HCl in water, phosphate buffer or phosphate buffered saline may be used. However, the neutralizing step may also simultaneously occur with purification, such as in the course of dialysis.

Optionally, a swelling step may be carried out before purification (and after the neutralizing step, if present) in which the hydrated, crosslinked HA gel is allowed to swell in an aqueous solution (e.g. in a phosphate buffer, especially in a phosphate buffered saline) for a given time (e.g., 6 h to 50 h) and temperature (e.g., 2° C. to 8° C.). Alternatively, the swelling is not a separate step but may occur concurrently with the purification, such as during dialysis.

As mentioned above, the crosslinked HA-based composition obtained from step (b) is generally purified, e.g., by dialysis. In one variation of the method according to the second aspect of the present invention, the method may further comprise, after step (b), step (c) of dialyzing the crosslinked HA-based composition, wherein the dialysis is carried out at elevated temperatures of, e.g., at least 10° C., at least 15° C., at least 20° C., at least 25° C., or at least 30° C., particularly at a temperature of at least 35° C. or at least 40° C., more particularly at a temperature of at least 45° C. or at least 50° C. This dialysis step at elevated temperature corresponds to the dialysis step explained and described in detail above in connection with the first aspect of the present invention. Thus, all definitions and explanations given above equally apply here in relation to the method according to the second aspect of the present invention.

The method may further comprise, after step (c), the step (d) of sterilizing the crosslinked HA-based composition. This step is commonly accomplished by sterilizing with moist heat as explained in connection with the method according to the first aspect of the present invention, e.g., by autoclaving under appropriate conditions, such as at a temperature of 121 to 130° C. for 1 to 20 minutes, e.g. at 121° C. for 5 minutes.

Moreover, as explained above in connection with the method according to the first aspect of the invention, the dermal filler may optionally contain one or more additional compounds, including non-crosslinked HA, crosslinked and/or non-crosslinked polysaccharides other than HA, local anesthetics such as lidocaine, antioxidants, amino acids, metal salts, hydroxyapatite particles, polyols, and vitamins. These optional compounds may be added to the crosslinked HA gel at any appropriate process stage before final sterilization, but are preferably added after dialysis and before sterilization. The explanations and definitions given above with respect to these additional compounds apply, mutatis mutandis, also to the method according to the second aspect of the present invention.

In a third aspect, the present invention relates to a hyaluronic acid (HA) dermal filler prepared by the method according to the first aspect and/or the second aspect of the present invention.

The dermal filler is preferably a dermal filler preparation that has been sterilized by moist heat, as described herein above. The conditions of moist heat sterilization are preferably selected such that the resulting dermal filler is sterile and its rheological properties are not unduly decreased due to the exposure to high temperatures. For example, the modulus of elasticity (G') after sterilization is preferably not decreased by more than 60%, 50% or 40%, and more preferably not decreased by more than 30% or 20%, compared to the G' value before sterilization.

In a fourth aspect, the present invention relates to a kit comprising a hyaluronic acid (HA) dermal filler according to the third aspect of the present invention, or prepared in accordance with the method of the first aspect or second aspect of the present invention, and optionally instructions for use.

The kit preferably comprises a syringe prefilled with the dermal filler of the present invention. The instructions for use preferably prescribe that the intended use of the kit is for cosmetic applications, in particular those described herein. The term "cosmetic" is interchangeably used herein with the term "aesthetic".

In a fifth aspect, the present invention relates to the use of a hyaluronic acid (HA) dermal filler according to the present invention for cosmetic applications.

Exemplary cosmetic applications in accordance with the present invention include, but are not limited to, augmenting or filling of wrinkles and lines of the skin, in particular of facial lines and facial wrinkles (e.g., glabellar lines, nasolabial folds, chin folds, marionette lines, buccal commissures, peri-oral wrinkles, peri-lip wrinkles, and crow's feet). Other exemplary cosmetic applications include treating the perioral region, facial asymmetries, jawlines, chin, cheeks, nose, lips, and infraorbital region as well as improving skin hydration and/or skin texture.

In a sixth aspect, the present invention relates to a method for replacing or filling of a biological tissue or increasing the volume of a biological tissue for cosmetic purposes, in particular for cosmetic treatments of skin lines and wrinkles, comprising administering to a subject in need thereof an effective amount of the hyaluronic acid (HA) dermal filler according to the present invention.

The term "effective amount", as used herein, is generally intended to refer to the amount of the dermal filler composition sufficient to effect beneficial or desired cosmetic (aesthetic) results. A "subject" in the sense of the present invention is any individual or patient, usually a human, in need of a treatment of a particular condition.

The dermal filler composition of the present invention is generally administered by injection, more specifically by subcutaneous or intradermal injection, using techniques known in the art such as the serial puncture technique. In particular, the dermal filler composition may be injected into the dermis and/or the subcutis, preferably into the deep dermis and/or upper subcutis.

EXAMPLES

The following non-limiting examples further illustrate the present invention.

Example 1

Increased Elastic Modulus (G') by Using Phosphate Buffer During Synthesis

HA gels were prepared by adding dry HA fibers (Mw=2.5 to 2.9×10$^6$ Da) into water (gel A), a low phosphate buffer (gel B) or a high phosphate buffer (gel C) (see TABLE 1).

TABLE 1

| Component | Low phosphate buffer (1.52 mM PO$_4^{3-}$; 190 mOsm) | High phosphate buffer (45 mM PO$_4^{3-}$; 190 mOsm) |
| --- | --- | --- |
| NaH$_2$PO$_4$•2H$_2$O | 0.045 g | 2.319 g |
| Na$_2$HPO$_4$•2H$_2$O | 0.22 g | 5.378 g |
| NaCl | 5.7 g | 2.066 g |
| H$_2$O | 994.035 g | 990.24 g |
| Total | 1000 g | 1000 g |

The resulting mixtures were mixed two times for 60 min at 250 rpm and 50° C. The temperature was then set to 5° C., a NaOH solution was added, and the mixtures were mixed for 30 to 40 min at 250 rpm. Next, a 6% BDDE solution of NaOH in water (gel A), low phosphate buffer (gel B) or high phosphate buffer (gel C) was added, followed by mixing for 10 to 15 min at 500 rpm.

The resulting reaction mixtures had a pH of at least 13, a HA concentration of 117 mg/g and a BDDE amount of 6 wt. %, based on the weight of dry HA (7 mg/g). The low and high phosphate reaction mixtures further contained $NaH_2PO_4 \cdot 2H_2O$ (0.04 mg/g and 1.95 mg/g, respectively), $Na_2HPO_4 \cdot 2H_2O$ (0.19 mg/ml and 4.53 mg/ml, respectively), and NaCl (4.80 mg/g and 1.74 mg/g, respectively).

Then, the temperature was set to 34° C., and slow mixing (100 rpm) was performed until the set temperature of 34° C. was reached. The reaction mixtures were allowed to crosslink for 240 to 250 min at 34° C. The resulting cake products were homogenized and neutralized to pH 7.0 to 7.4 using a solution of HCl in water (gel A), low phosphate buffer (gel B) or high phosphate buffer (gel C). The neutralized gels were then extruded through a first screen, mixed for 60 min at 250 rpm and 5° C., extruded through a second screen, and then extruded through a third screen into dialysis membranes.

The dialysis membranes were placed into a container of low phosphate dialysis buffer (for all samples, i.e. gels A, B and C) and dialyzed for 40 h at a temperature of 50±1° C. with three buffer exchanges. The low phosphate dialysis buffer corresponds to the low phosphate buffer defined above, except that the NaCl content was adapted from 5.7 g/l to 8.5 g/l to increase the osmolality to a physiological value of 270 mOsm/kg. It is noted that the dialysis may also be performed at lower temperatures (e.g., 4° C. or 20° C.), although for a prolonged time, to obtain the same or similar dialysis effects.

Finally, the gels were then removed from the dialysis membranes and homogenized by screening. The HA concentration of the final gels was 23 mg/g. The gels were then filled into 1 ml BD glass syringes and sterilized by moist heat for 4 min at 127° C., resulting in gels A, B and C.

The rheological parameters (elastic modulus (G'), loss tangent (tan δ=G"/G'), and complex viscosity (η*)) were determined using an Anton Paar rheometer (MRC 302), equipped with a plate and plate geometry of 35 mm diameter and a gap of 1 mm, at a frequency range of 10 to 0.1 Hz with a shear stress of 5 Pa. The rheological values indicated are at 1 Hz. All measurements were performed at a temperature of 30° C. The results are summarized in TABLE 2.

TABLE 2

| Sample | Crosslinking reaction medium | Rheological parameters | | | | | |
|---|---|---|---|---|---|---|---|
| | | Before sterilization | | | After sterilization | | |
| | | $G'_{(1\,Hz)}$ [Pa] | tan(δ) (1 Hz) | $\eta^*_{(1\,Hz)}$ [Pa·s] | $G'_{(1\,Hz)}$ [Pa] | tan(δ) (1 Hz) | $\eta^*_{(1\,Hz)}$ [Pa·s] |
| Gel A | Water | 306 | 0.26 | 50 | 109 | 0.46 | 19 |
| Gel B | Low phosphate buffer | 229 | 0.31 | 51 | 141 | 0.41 | 32 |
| Gel C | High phosphate buffer | 304 | 0.26 | 50 | 170 | 0.39 | 29 |

Example 2

Improvement of G' by Addition of LiCl

A HA gel (gel D) was prepared as described above for gel C using the high phosphate buffer (high P-buffer) in the crosslinking reaction. Another HA gel (gel E) was prepared in the same manner as for gel D, except that a buffer was used in the crosslinking reaction that was identical to the high phosphate buffer but additionally contained 0.03% (w/w) lithium chloride (LiCl). The results of the rheological measurements are shown in TABLE 3.

TABLE 3

| Sample | Crosslinking reaction medium | Rheological parameters | | | | | |
|---|---|---|---|---|---|---|---|
| | | Before sterilization | | | After sterilization | | |
| | | $G'_{(1\,Hz)}$ [Pa] | tan(δ) | $\eta^*_{(1\,Hz)}$ [Pa·s] | $G'_{(1\,Hz)}$ [Pa] | tan(δ) | $\eta^*_{(1\,Hz)}$ [Pa·s] |
| Gel D | High P-buffer | 336 | 0.16 | 54 | 230 | 0.22 | 38 |
| Gel E | High P + LiCl-buffer | 395 | 0.13 | 63 | 261 | 0.18 | 42 |

As is evident from TABLE 3, the addition of LiCl in an amount of as low as 0.03% (w/w) surprisingly leads to a significant improvement of G'.

Thus, the results show that the rheological properties of a HA gel manufactured using a high phosphate crosslinking buffer (see Example 1) can be yet further enhanced by the presence of low amounts of an alkaline metal halide salt during crosslinking. This in turn allows the use of lower amounts of BDDE to achieve the same or similar rheological properties (e.g., G'), resulting in lower amounts of residual BDDE and degradation products thereof in the crosslinked HA gel product.

Example 3

Improved Removal of Residual BDDE

A HA gel (gel F) was prepared as described in Example 1, except that BDDE was used in an amount of 9% and the high phosphate buffer defined in TABLE 1 was used as dialysis buffer. The produced crosslinked HA gel was filled into cellulose membranes (Spectrum, USA) having a molecular weight cut-off (MWCO) of 12-14 kDa, and a length of 80 cm and a width of 45 mm. The filling ratio was 8.0 to 8.3 g gel/cm membrane.

The filled membranes were then placed into a dialysis tower (Spectrum, USA) filled with 6-7 l of the above-mentioned high phosphate buffer, connected to a reservoir tank filled with 30 l of the high phosphate buffer. The buffer was continuously circulated through a heated water bath using a peristaltic pump to adjust the temperature as desired and exchanged two times during dialysis. The dialysis was carried out for 40 h at a temperature of 40±1° C. (gel F1, four measurements) or 50±1° C. (gel F2; six measurements).

As a comparison, the HA gel is put into the same Spectrum cellulose membranes mentioned above with the same filling ratio and subjected to a standard static dialysis procedure. More specifically, the gel filled membranes were placed into a container filled with 10 l of said high phosphate buffer and dialyzed for 40 h at 5-8° C. The buffer was exchanged two times.

The BDDE content of the dialyzed gels was determined by gas chromatography (GC) according to standard procedures. The results are shown in TABLE 4.

TABLE 4

| Gel | Sample | Temp. | Dialysis method | BDDE content [ppm] Single values | Mean |
|---|---|---|---|---|---|
| Gel F0 | 1 | 5-8° C. | Standard static dialysis | 270 | 270 |
| Gel F1 | 2 | 40° C. | Isothermic flow dialysis | 37 | 36 |
| | 3 | | (dynamic dialysis) | 34 | |
| | 4 | | | 36 | |
| | 5 | | | 35 | |
| Gel F2 | 6 | 50° C. | | 12 | 11 |
| | 7 | | | 11 | |
| | 8 | | | 12 | |
| | 9 | | | 9 | |
| | 10 | | | 15 | |
| | 11 | | | 8 | |

As can be seen from TABLE 4, the flow dialysis at temperatures of 40° C. and 50° C. resulted in drastically reduced BDDE contents (reduction by about 87% and 96%, respectively) compared to standard dialysis. Notably, increasing the temperature from 40° C. to 50° C. resulted in a further reduction of BBDE content from 36 ppm to 11 ppm, corresponding to a decrease of about 69%. Similar results were also obtained for standard dialysis when comparing the residual BDDE content after dialysis at 40° C. and 5-8° C. as well as after dialysis at 50° C. and 40° C. (results not shown).

Surprisingly, the gels dialyzed at elevated temperatures of 40° C., and even at 50° C., did not show any signs of enhanced degradation, as can be deduced from the progress of rheological properties (G', tan δ, η*), extrusion force, pH and osmolality over time. The rheological properties over time followed a typical profile for HA gels and remained within the specification.

Thus, the high temperature dialysis of the present invention offers the advantages of an increased rate and efficiency of dialysis. This allows the dialysis time to be shortened, resulting in an improved manufacturing process of HA gels.

The invention claimed is:

1. A method for preparing a hyaluronic acid (HA) dermal filler comprising:
   (a) providing a composition comprising water, non-cross-linked HA and 1,4-butanediol diglycidyl ether (BDDE), and
   (b) reacting the composition under conditions that allow crosslinking the non-crosslinked HA to form a crosslinked HA-based composition in the form of a gel,
   wherein said composition further comprises at least one alkali metal halide salt and phosphate, the phosphate being provided by at least one phosphate salt and optionally phosphoric acid, wherein the phosphate salt is an alkali metal phosphate salt, an alkaline earth metal phosphate salt, or a combination thereof,
   wherein the amount of the at least one alkali metal halide salt in the composition is from 0.01 wt. % to less than 0.45 wt. %, and the amount of phosphate in the composition is from 0.001 wt. % to 5 wt. %, the amount of phosphate being calculated as the total amount of said at least one phosphate salt and said optional phosphoric acid,
   wherein the alkali metal halide salt is lithium chloride, and
   wherein the alkali metal phosphate salt is a salt of phosphate and lithium, sodium, potassium, or a combination thereof, and the alkaline earth metal phosphate salt is a phosphate salt of magnesium, calcium, or a combination thereof.

2. The method of claim 1, further comprising, after (b):
   (c) dialyzing the crosslinked HA-based composition, wherein the dialysis is carried out at a temperature of at least 20° C.

3. The method of claim 2, further comprising, after (c):
   (d) sterilizing the crosslinked HA-based composition.

4. The method of claim 1, wherein the amount of the at least one alkali metal halide salt in the composition is from 0.01 wt. % to less than 0.1 wt. %, and/or wherein the amount of phosphate in the composition is from 0.1 wt. % to 2 wt. %, the amount of phosphate being calculated as the total amount of said at least one phosphate salt and said optional phosphoric acid.

5. The method of claim 1, further comprising, after (b):
   (c) dialyzing the crosslinked HA-based composition, wherein the dialysis is carried out at a temperature of at least 30° C.

6. The method of claim 1, wherein the amount of the at least one alkali metal halide salt in the composition is from 0.03 wt. % to 0.4 wt. %.

7. The method of claim 1, wherein the amount of phosphate in the composition is from 0.01 wt. % to 2.5 wt. %, the amount of phosphate being calculated as the total amount of said at least one phosphate salt and said optional phosphoric acid.

8. The method of claim 1, wherein the phosphate salt is an alkali metal phosphate salt.

9. The method of claim 1, wherein the phosphate salt is a salt of phosphate and sodium.

* * * * *